US007218393B2

(12) United States Patent
Sharpe et al.

(10) Patent No.: US 7,218,393 B2
(45) Date of Patent: May 15, 2007

(54) ROTARY STAGE FOR IMAGING A SPECIMEN

(75) Inventors: James Alexander Sharpe, Edinburgh (GB); Paul Ernest Perry, Edinburgh (GB)

(73) Assignee: Medical Research Council, London (GB)

( * ) Notice: Subject to any disclaimer, the term of this patent is extended or adjusted under 35 U.S.C. 154(b) by 193 days.

(21) Appl. No.: 10/479,111

(22) PCT Filed: May 21, 2002

(86) PCT No.: PCT/GB02/02373

§ 371 (c)(1),
(2), (4) Date: May 14, 2004

(87) PCT Pub. No.: WO02/095476

PCT Pub. Date: Nov. 28, 2002

(65) Prior Publication Data

US 2004/0207840 A1    Oct. 21, 2004

(30) Foreign Application Priority Data

May 22, 2001 (GB) .............................. 0112392.6

(51) Int. Cl.
*G01N 21/01* (2006.01)
(52) U.S. Cl. ..................................... 356/244

(58) Field of Classification Search ................ 250/573, 250/576, 201.3; 356/239.1, 31, 138, 244, 356/440, 73, 246, 245, 30; 382/255, 108, 382/296
See application file for complete search history.

(56) References Cited

U.S. PATENT DOCUMENTS

| 4,136,961 | A | * | 1/1979 | Young, II | ................ 356/239.1 |
| 4,563,883 | A | | 1/1986 | Sitte | |
| 5,422,718 | A | | 6/1995 | Anderson | |
| 5,680,484 | A | | 10/1997 | Ohyama | |
| 5,710,625 | A | | 1/1998 | Neumann | |
| 5,818,637 | A | | 10/1998 | Hoover | |

* cited by examiner

*Primary Examiner*—Layla G. Lauchman
*Assistant Examiner*—Tri Ton
(74) *Attorney, Agent, or Firm*—Barnes & Thornburg LLP

(57) ABSTRACT

A rotary stage (10) for use in optical projection tomography includes a stepper motor (42) with a rotatable vertical shaft (44) the lower end of which carries a specimen (28) to be imaged so that the specimen is rotated about a substantially vertical axis. The stepper motor (42) is mounted on a table (34) the position of which is accurately adjustable in tilt and in vertical position to ensure that the rotational axis of the specimen is perpendicular to the optical axis (29). The specimen (28) rotates within a stationary chamber (26) and the rotary stage is used with a microscope which provides a three-dimensional image of the specimen.

17 Claims, 10 Drawing Sheets

Fig.5(a)  Fig.5(b)  Fig.5(c)  Fig.5(d)
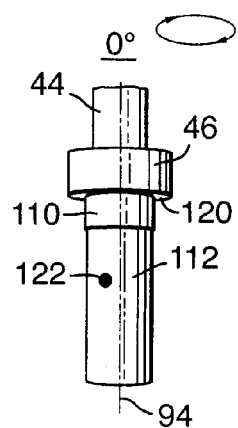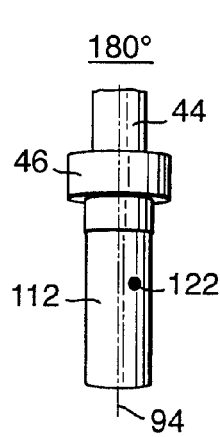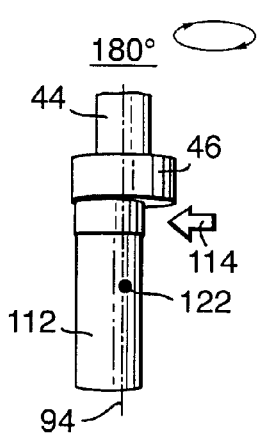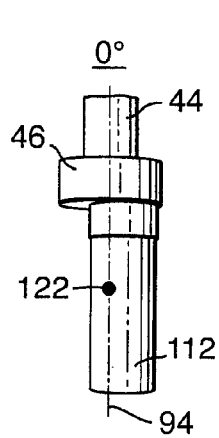
Fig.6(a)  Fig.6(b)  Fig.6(c)
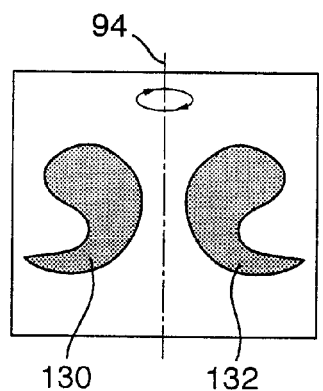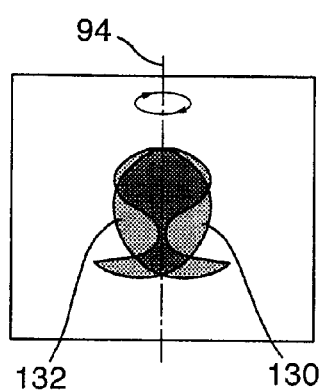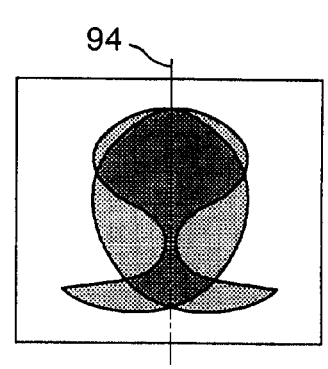

ROTARY STAGE FOR IMAGING A SPECIMEN

FIELD OF THE INVENTION

This invention concerns a rotary stage for imaging a specimen, and a method of obtaining an image of a specimen. The invention is particularly, but not exclusively, concerned with optical projection tomography and three dimensional microscopy.

BACKGROUND OF THE INVENTION

Optical imaging apparatus for producing three-dimensional images of samples by optical projection tomography is known, see for example U.S. Pat. No. 5,680,484. The optical apparatus disclosed in this prior art patent takes a series of digital images of a sample from different angles. These images are fed into an algorithm which use a mathematical transform to reconstruct a three dimensional image. In U.S. Pat. No. 5,680,484 the specimen is held within a transparent tube which is supported at two points so as to be substantially horizontal, and the tube is rotated using a stepper motor and driving belt to allow different parts of the specimen to be imaged. Light refraction from the tube affects signal quality and use of the tube places a severe constraint on the maximum size of specimen which can be imaged. The apparatus disclosed in this prior art patent has several limitations which affect the potential uses of this imaging technique, in particular it is difficult to introduce the sample into the hollow cylindrical tube, and difficult to adjust the position of the sample.

It is an aim of the present invention to provide an apparatus and method which overcome at least some of the aforementioned problems.

SUMMARY OF THE INVENTION

In accordance with one aspect of the present invention, there is provided a rotary stage for use in imaging a specimen from a plurality of directions, the rotary stage comprising specimen support means including a rotatable member operative to rotate a specimen to be imaged about a vertical or substantially vertical axis of rotation transverse to an optical axis along which light is emitted from the specimen, wherein the specimen support means is disposed above a stationary imaging chamber for receiving the specimen immersed in optical imaging fluid within the chamber.

The rotary stage may be used with a separate microscope and associated hardware and software that allows three dimensional imaging of a specimen, such as a biological tissue. By having a specimen support means spaced from the microscope, the positioning of the specimen can be easily adjusted due to improved accessibility of the specimen holder. With an elongate specimen, the longest axis of the specimen is substantially parallel to gravity when held within the specimen support means. This allows the specimen to be held at one point only, again assisting with location of the specimen within the specimen support means, and avoids deflection of the specimen through gravitational effects, as such deflection can cause unwanted distortion of the specimen shape and affect the accuracy and resolution of the image obtained.

By having a stationary chamber separated from the rotational part of the stage, the chamber shape is not limited to a rotationally symmetric shape. Preferably the chamber has at least one planar face on which light impinges to image the specimen. Use of a flat planar face with no imperfections or undulations ensures that image distortion due to refraction of light is reduced. The chamber may be formed as a transparent hollow cuboid and arranged such that two opposing sides of the cuboid are substantially perpendicular to the optical axis along which light is emitted from the specimen so that a large cross-sectional area is presented to the optical axis. The selection of such a chamber with a square cross-section ensures that the amount of light refracted before passing through the specimen is substantially reduced over prior art cylindrical rotating chambers and thus image quality is improved. One wall or face of the chamber may be shaped so as to refract light in a desired way, for example to provide a magnifying effect.

The rotary stage may further comprise a pivotally mounted adjustment means, such as a lever, having a spigot extending therefrom, the spigot being arranged in use so as to engage with a specimen to alter its position relative to the axis of rotation.

The rotary stage may further comprise a prism positioned so as to receive light after the latter has illuminated the specimen, the prism acting to deflect light through 90° to enable the light to be received by a microscope with a vertical optical axis. By using a prism, the optical path to the microscope does not need to be straight, and thus modification of existing microscopes is not needed for use with a rotary stage in accordance with the present invention.

The rotatable member of the specimen support means may be carried on an adjustable platform, the position of which relative to the horizontal is variable. This allows the axis of rotation to be adjusted relative to an optical axis so that if required a 90° angle is set between the optical axis and the axis of rotation. This is particularly useful for three dimensional imaging.

The adjustable platform is preferably vertically adjustable so as to raise and lower the rotating member relative to the optical axis, so allowing a specimen to be lowered into or out of an optical path of light.

Preferably the rotatable member is formed to enable the specimen to be hung, suspended or to downwardly depend from the lower end of the rotatable member. Where a specimen is appropriately prepared with a magnetisable metal mount, attachment of the specimen to the specimen support means is then straightforward, just relying on magnetic attraction and not on a delicate fixing. This is of advantage as typically the specimens are rather small and delicate, usually with a diameter in the range 1–20 mm, and securing them in a holder using a screw thread can be complicated.

In accordance with another aspect of the present invention, there is provided a method of obtaining an image of a specimen, the method comprising rotating the specimen about a vertical or substantially vertical axis of rotation transverse to an optical axis along which light is emitted from the specimen, wherein the rotating specimen is immersed in fluid within a stationary optical chamber.

BRIEF DESCRIPTION OF THE DRAWINGS

The invention will now be described, by way of example, with reference to the accompanying drawings in which:

FIGS. 5(a), 5(b), 5(c) and 5(d) illustrate attachment of a specimen to the specimen support means and alignment of a region of interest;

FIGS. 6(a), 6(b) and 6(c) are schematic diagrams used to explain resolution of the apparatus;

DETAILED DESCRIPTION

Figure 1:
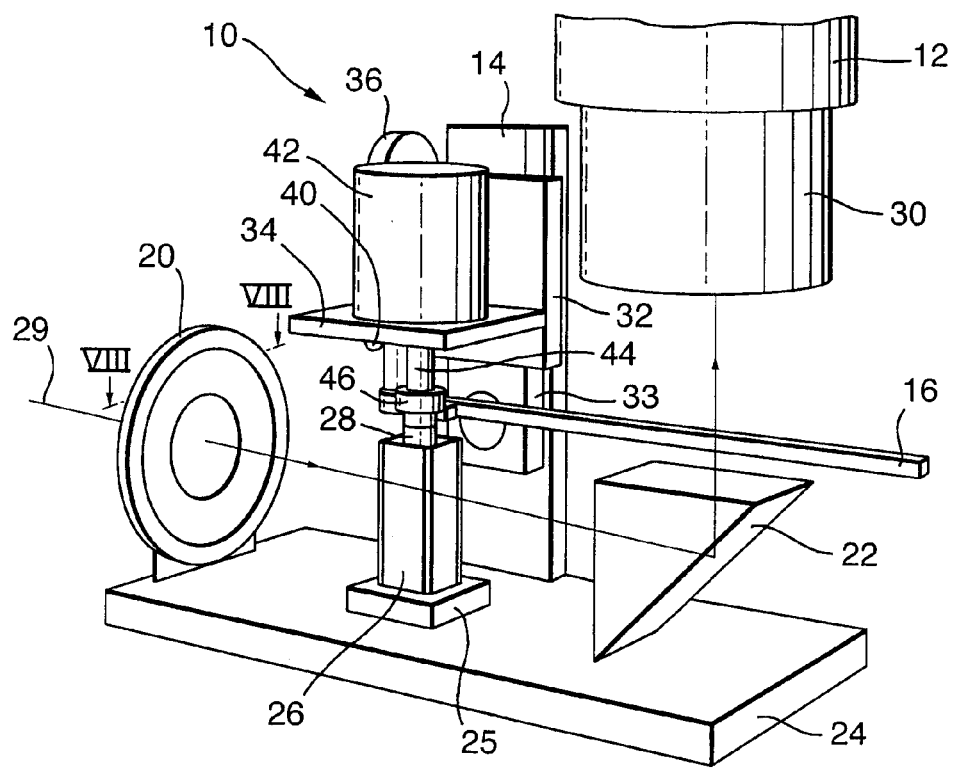
FIG. 1 is a perspective view of optical imaging apparatus comprising a rotary stage in accordance with the present invention together with a microscope.

FIG. 1 shows optical imaging apparatus in the form of an OPT scanner comprising a rotary stage 10 and a long working distance or dissecting microscope 12, separate from the rotary stage 10. The rotary stage 10 has a support 14, a pivotally mounted lever 16, an iris and optical diffuser 20, and a quartz prism 22. The support 14, iris and diffuser 20, and prism 22 are fixed to a base 24 of the stage 10, as is a holder 25 for receiving a transparent chamber 26, or cuvette, of a generally cuboid shape. The cuvette 26 contains a fluid with suitable optical properties for imaging a specimen 28 suspended within the cuvette, an appropriate fluid being a mixture of benzyl alcohol and benzyl benzoate. This apparatus can be used for brightfield, darkfield and fluorescence imaging but is particularly appropriate where a three dimensional (3D) image of the specimen is created from a series of images taken at different angles, and for specimens too large to be imaged by confocal microscopy.

Light passes along optical axis 29, passing through the centre of the iris and diffuser 20, and through the specimen 28 and is deflected through right angles by the prism 22 to enter an objective 30 of the microscope 12. As the microscope has a large working distance, enough space is available for the prism 22 to rest beneath the microscope objective 30. Using a prism allows a vertically oriented microscope to image the specimen. However the prism 22 can be omitted where the microscope objective is parallel to the optical axis. The iris and diffuser 20 control the amount of light passing from a light source (not shown) to reach the specimen 28 and provide even illumination.

Figure 4A:
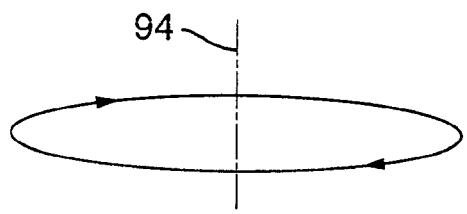
FIGS. 4(a) and 4(b) are schematic diagrams used to illustrate the most appropriate working configuration of the apparatus.
Figure 4B:
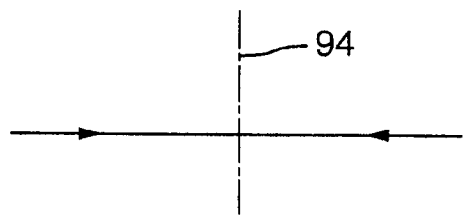

The support 14 carries a circular boss on which is pivotally mounted, about an axis 90 (FIG. 4), a tilting plate 33 upon which is slidable, upwards and downwards, a plate 32. The plate 32 carries an adjustable platform 34 cantilevered horizontally from the plate 32. The angle of the platform 34 can be altered relative to the horizontal using a tilt adjuster 36 and the vertical position of the platform 34 can be varied by means of a vertical adjuster 40. A stepper motor 42 is mounted on the platform 34, with a rotatable motor shaft 44 of the motor extending through the platform 34. A magnet 46 (a permanent magnet or an electromagnet) is attached to the lower end of the shaft 44 and carries the specimen 28 to be imaged. The manner in which the specimen is attached to the magnet will be described later with reference to FIG. 5. The stepper motor 42 rotates the shaft 44 with a step size of 0.9 degrees, providing up to 400 imaging positions of the specimen. A series of digital images of the elongate specimen 28 is taken by indexing the shaft 44 to its successive rotational positions, and thus positioning the specimen in successive rotational positions whilst the specimen is suspended within the cuvette 26, the cuvette remaining stationary.

By mounting the stepper motor 42 with its axis of rotation vertical, the rod-like specimen 28 only needs to be secured at one point, typically its uppermost end, for controlled rotation of the specimen to occur. The specimen 28 is immersed in the liquid, supported from above by the magnet 46, by using the vertical adjuster 40 to lower the platform. This vertical orientation of the specimen and the rotational axis avoids the use of O-rings or other mechanical arrangements which would be necessary to connect the dry motor to the immersed specimen, and secondly it ensures that the specimen is not deflected off its axis of rotation by gravity as the elongate specimen has its major axis parallel to the force of gravity. Avoiding distortion effects to the specimen by having a vertically orientated specimen is particularly important for obtaining accurate 3D images, particularly for larger specimens. Use of a generally upright hollow cuboid as the imaging chamber 26 around the specimen 28 ensures that the surface area of the imaging liquid is limited, reducing evaporation of the liquid. In addition much larger specimens, typically 1–20 mm in diameter, can be imaged by using such a fixed chamber without loss of digital signal quality.

Figure 2:
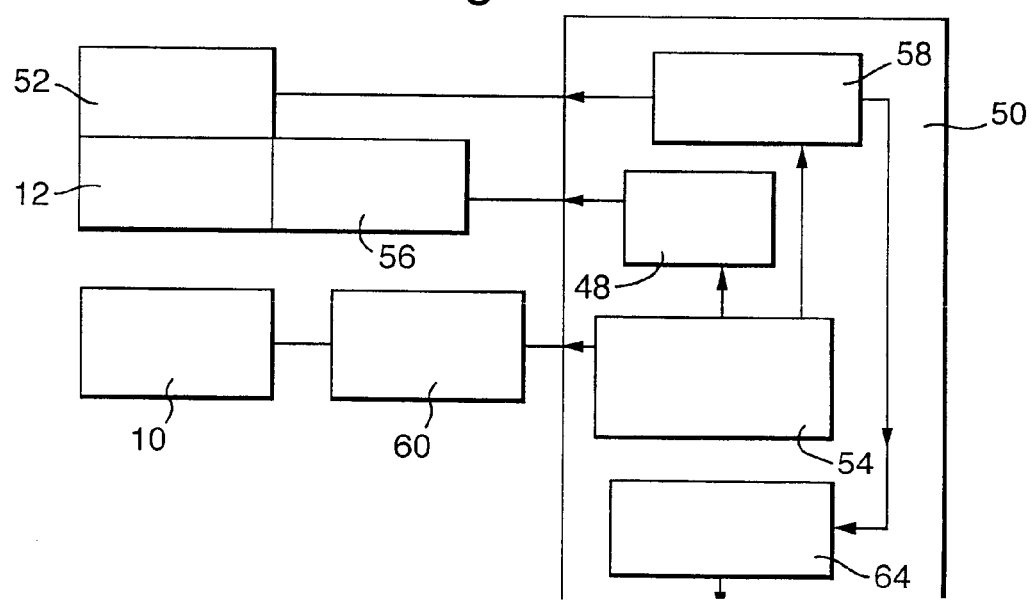
FIG. 2 shows a schematic illustration of how such imaging apparatus is controlled when acquiring digital images.

In use, a digital camera 52 (FIG. 2) is attached to the microscope 12 and produces a digital image of the specimen as imaged by the microscope from light that has travelled along the optical axis 29, and been transmitted through the chamber and specimen. A series of digital images are taken of the specimen from different angles and this digital information is fed into an algorithm which uses a mathematical formula to reconstruct the structure of the specimen in three dimensions. Typically the images are obtained using the control elements as set out in FIG. 2. Thus a computer 50 carrying digital image acquisition software is in two-way communication with the digital camera 52 attached to the microscope 12 which receives images from a specimen of interest. The computer 50 controls filter wheels 56 attached to the microscope 12 to alter the wavelength of radiation that is detected. The computer acquisition software is shown diagrammatically in FIG. 2 as software 58 to control image-capture from the digital camera, a program 54 to control the imaging software, the rotary stage and the filter wheel software, software 48 to control the filter wheels and software 64 to convert the image files into a 3D reconstruction. The computer is also in two-way communication with electronic control circuits 60 connected to the rotary stage 10 and controls the circuits 60 to adjust the orientation of the specimen as required during image capture of successive images. Once the digital images have been obtained, they are processed at 64 to produce a 3D reconstruction 66 of the specimen using mathematical processing, in a similar manner to the analysis described in U.S. Pat. No. 5,680,484.

If required, the computer can control the entire imaging process, undertaking image-processing to determine the size of the specimen, its alignment, whether it is in focus etc., and adjusting the specimen position before performing the rotational imaging. This complete automation of the imaging process is particularly desirable for large scale gene expression mapping projects in which many such devices could be run in parallel.

The circuitry 60 responsive to the computer to control the stepper motor 42 is commercially available for most popular computer systems. The circuitry 60 connects to the computer 50 and is responsive to signals from the computer 50 to control a variety of mechanical devices (stepper motors, solenoids etc.).

To create a 3D representation of the specimen, software performs the following functions: (1) determine the axis of rotation (through the symmetry which exists between each pair of images which were taken at 180 degrees to each other), (2) reorganise the stack of images into an orthogonal stack of projection images (in which image represents a single section through the specimen, viewed from all the different angles captured), (3) perform the mathematical processing on each projection image, to recreate that section through the specimen, (4) combine all the calculated section images into a 3D format. Reconstructions can be created both from transmitted light and from fluorescently-emitted light.

Now that the general apparatus and its use in data acquisition has been described, certain components of the imaging apparatus will be described in more detail.

Figure 3:
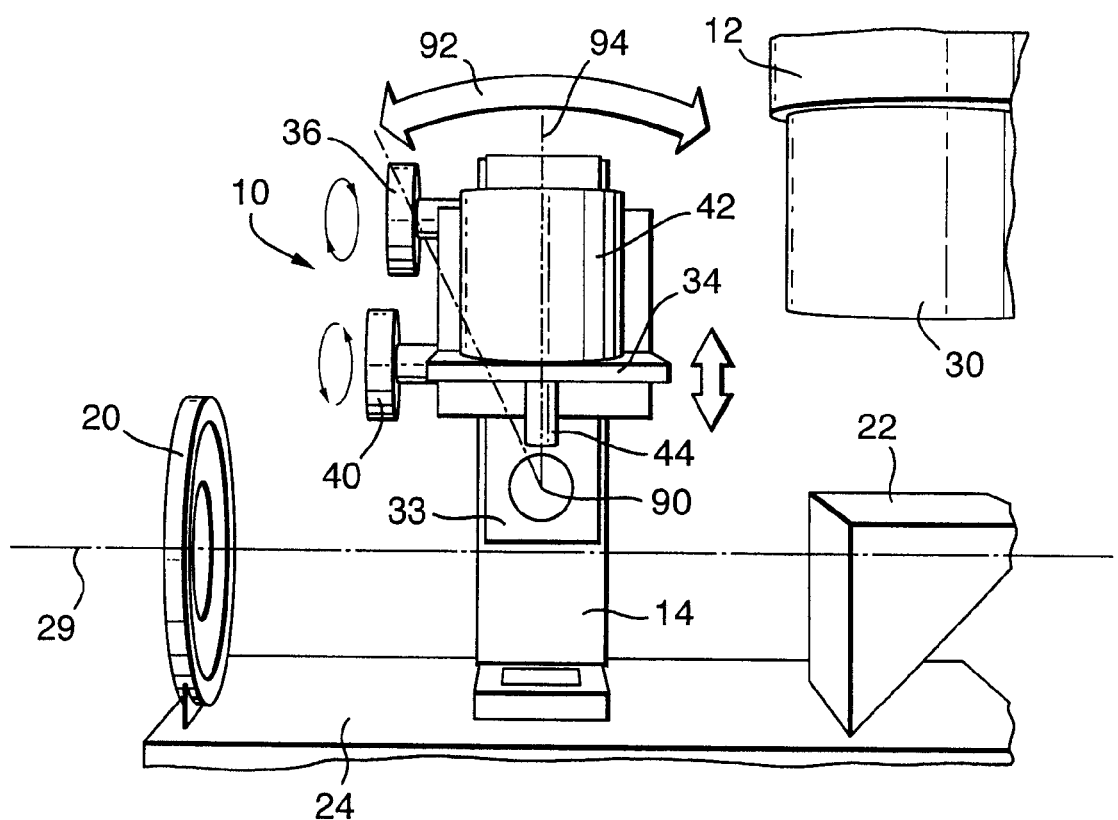
FIG. 3 shows a front perspective view of the apparatus.

A front view of the rotary stage 10 is shown in FIG. 3. The tilt adjuster 36 varies the angle of tilt of the platform 34 about the axis 90 which is below the lower end of the shaft 44 and is approximately at the height of the specimen so that tilt adjustment does not move the specimen substantially. The axis 90 may intersect the optical axis 29. Tilt adjustment (illustrated by the double-headed arrow 92 in FIG. 3) ensures that the rotational axis 94 of the stepper motor 42 is accurately perpendicular to the optical axis 29. Having adjusted the tilt of the platform 34, the position of the platform 34 relative to the base 24 is adjusted using the vertical adjuster 40 which uses a rack and pinion arrangement to raise and lower the platform 34 in the adjusted direction of the rotational axis 94. By using the vertical adjuster 40, a specimen carried on the magnet attached to the end of the shaft 44 can be lowered a required depth into the imaging chamber for imaging and raised out of the chamber once imaging has been performed. The vertical position of the specimen during imaging an also be altered in this way if required. In the raised position of the shaft, specimens can be loaded into or out of the rotary stage.

When the apparatus is set up, it is aligned such that the optical axis of the microscope passes through the prism, and through the centre of the imaging chamber. However, at high magnification the alignment can need adjusting as the specimen becomes slightly displaced away from the centre of the field-of-view. The raising/lowering mechanism mentioned above can be adjusted to correct for this misalignment in the vertical direction.

Whilst much imaging of the specimen can be undertaken by having the rotational axis approximately perpendicular to the optical axis, 3D reconstruction of the specimen using the mathematical processing will be of very poor quality unless the angle between the optical axis and the rotational axis is exactly 90°. The tilt adjuster 36 allows the axis of rotation 94 to be tilted slightly so as to ensure the angle is exactly 90°. The tilt adjuster 36 typically relies upon a screw-thread mechanism to urge the platform 34 to one side. A calibration sample is used to adjust the angle of tilt, with the calibration sample containing a number of small particles whose trajectories can be monitored on a computer screen while the shaft rotates. If the axis of rotation is not perfectly perpendicular to the optical axis, the trajectory of the particle appears as an ellipse, see FIG. 4(*a*) which shows the view along the optical axis as the shaft rotates about the axis 94. When the axis is correctly aligned, the particle is seen to move from side to side, with no vertical component to the motion, see FIG. 4(*b*).

FIG. 5 shows the magnetic mounting system used which relies upon magnetic attraction between a metal disc 110 attached to a specimen 112 and the cylindrical magnet 46 permanently attached to the lower end of the rotatable shaft 44 of the stepper motor 42. Each specimen has a small magnetisable metal disc glued at one end during specimen preparation. The disc is then attached to the magnet when imaging is to be undertaken and the specimen supported as a result of the magnetic attraction between the disc and the magnet. As the disc 110 and specimen 112 are relatively light, the magnet does not need to be strongly magnetised to support their weight. One advantage of the magnet system over, for example, a screw-in system, is that the small size of the disc and specimen necessitates handling with forceps or tweezers. Placing the mount or disc 110 onto a magnet is straightforward with forceps, whereas screwing it into an attachment is not. Another advantage is that the position of the specimen relative to the axis of rotation can be readily adjusted by sliding the mount 110 across the magnet surface 120. Also many specimens can be pre-prepared with a disc attached, and then quickly fitted into the device for imaging when required.

Certain liquids used in the chamber for sample imaging are toxic and corrosive to plastic, and where this is the case, the specimens are best handled using forceps. The magnetic attachment system is then of advantage as the specimens need only be held under the magnet to become securely attached. It is equally easy to remove each specimen after imaging.

To maximise the resolution of the images, a region of interest 122 in a specimen 112 must be centred on the axis of rotation 94, i.e. not move as the shaft rotates. If the region of interest, or the whole specimen, is off-centre and oscillates from side-to-side during a rotational image capture, then the magnification necessary to keep it in view will be low. This is illustrated in FIG. 6(*a*). The two shapes 130, 132 represent the specimen 112 during rotation, at its most extreme positions to the left and right. When the specimen 112 is perfectly centred, it spins on its own axis, see FIG. 6(*b*). This presents a smaller width across the field-of-view, and so the magnification can be increased to provide an image with higher resolution, see FIG. 6(*c*).

Adjustment of the specimen 112 relative to the axis of rotation 94 is simplified by the magnetic attachment. By pushing on the disc 110, the centre of the disc can be offset relative to the rotational axis 94. In FIG. 5(*a*) the region of interest 122 within the specimen 112 is not centred on the axis of rotation but rather is displaced to the left. If the motor shaft is rotated through 180°, the region of interest 122 is now visible on the right hand side of the axis of rotation, see FIG. 5(*b*). Because the magnet 46 allows the metal mount 110 to slide along it in any direction, without becoming unattached, a push from the side by the lever 16 (indicated by arrow 114 in FIG. 5(*c*) is able to position the specimen so that the region of interest 122 is centred on the axis of rotation, see FIG. 5(*c*). A further rotation of 180° shows that now the whole specimen 112 oscillates from side-to-side while the region of interest remains centred, see FIG. 5(*d*).

Adjustment of the specimen in this way is usually undertaken whilst observing images of the rotating specimen on a computer screen.

Figure 7A:
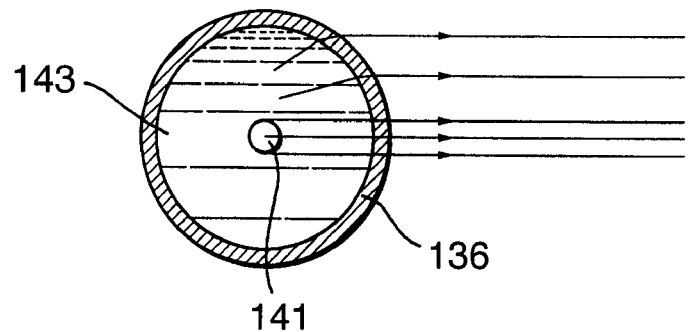
FIG. 7(a) shows a cross-section through a prior art specimen containing tube, with FIGS. 7(b) and 7(c) showing two specimen chambers as used in the present invention.
Figure 7B:
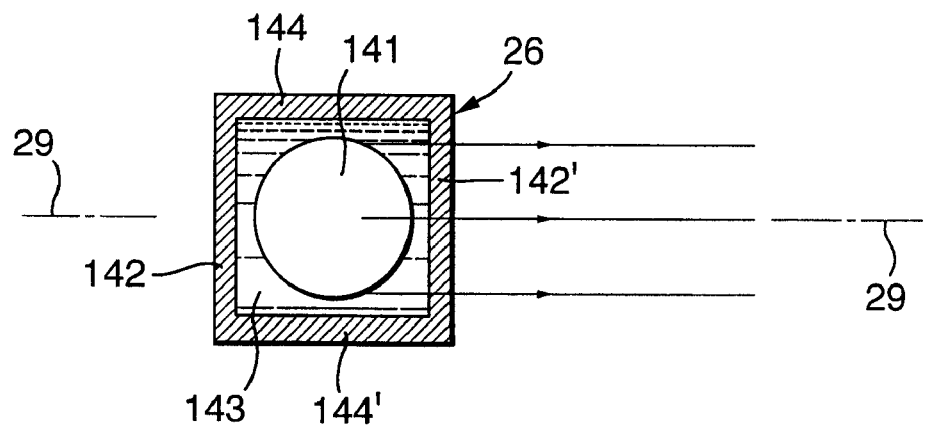

The imaging chamber 26 as shown in FIG. 1 will now be described in more detail with reference to FIG. 7. By having a fixed specimen chamber that does not rotate with the specimen during imaging, the chamber does not need to be cylindrical to maintain a constant optical path during rotation, as for the system described in U.S. Pat. No. 5,680,484. A comparison of prior art tube 136 and the chamber used in the present invention is shown in FIG. 7, FIG. 7(a) showing a cross-section through the prior art cylindrical tube 136 (which is suspended horizontally), and FIG. 7(b) showing the chamber 26 used in the present embodiment. The imaging chamber 26 is chosen to be generally cuboid and to be square in cross-sectional shape, and is made from quartz, glass or other suitably transparent material. Each chamber/tube contains a specimen 141 bathed in liquid 143 with suitable optical properties to allow imaging of the specimen. The flat sides 142, 142', 144, 144' of chamber 26 reduce refractive distortion of the image and allow larger specimens to be imaged. This is because the mutually parallel walls 142, 142' of the square cross-section chamber are aligned perpendicular to the optical axis 29 and provide a greater imaging area over which non-refraction of light occurs than for the circular tube 136, which only has a very small part of its circumference at normal incidence to the light. Thus a good image can be formed across a width of more than 10 mm for the chamber 26, improving the amount of signal received from the sample and reducing distortion due to refraction.

Figure 7C:
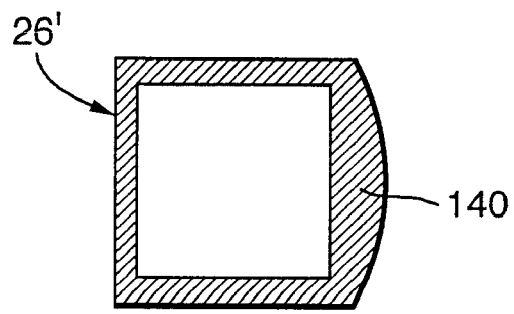

FIG. 7c illustrates a modification of the sample chamber of FIG. 7b. In FIG. 7c, the sample chamber 26' has a square internal cross-section but one wall 140 is shaped to provide a plano-convex lens to refract light leaving the chamber. The shaping causes a desired refraction, in the case of FIG. 7c a magnifying effect.

Figure 8A:
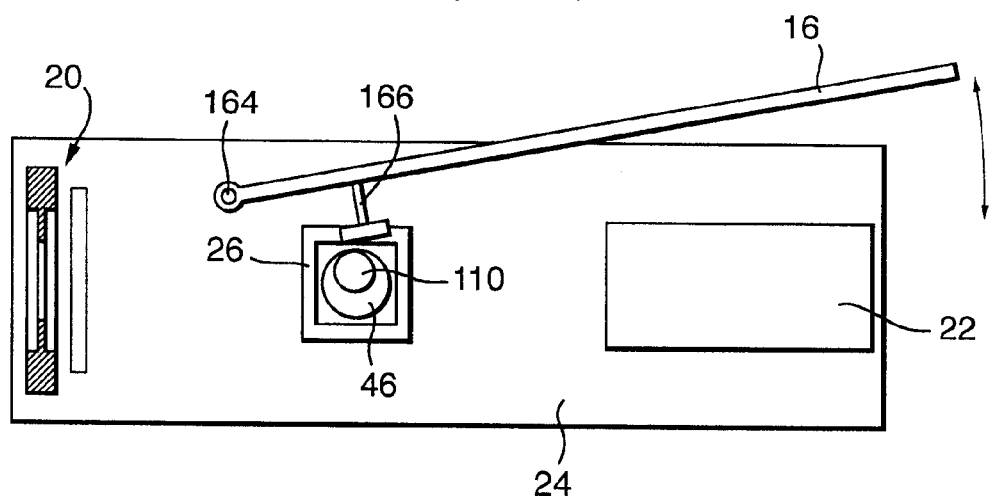
FIGS. 8(a) and 8(b) show a partial plan view along line VIII—VIII of FIG. 1, illustrating use of a pivotally mounted lever to adjust specimen position.
Figure 8B:
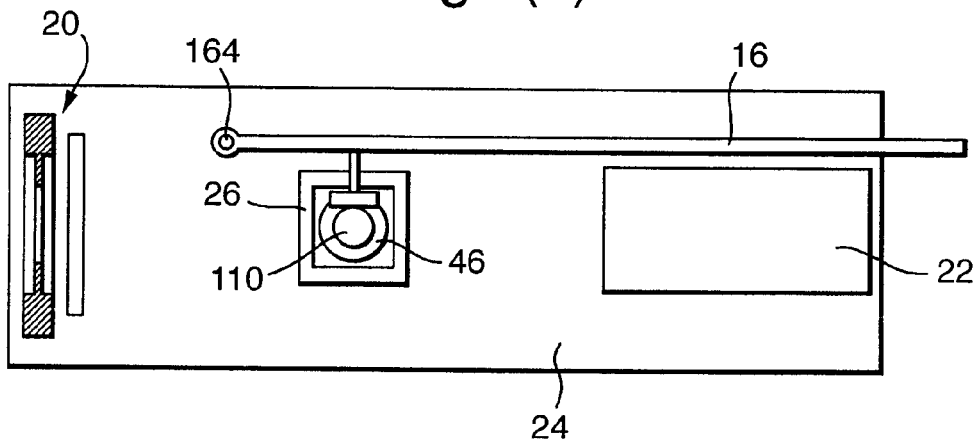

The lever 16 shown in FIG. 1 is now described in more detail with reference to FIG. 8, which shows a plan view along line VIII—VIII of FIG. 1. FIG. 8(a) shows the lever 16 in its usual position, pushed away from the magnet 46 and metal specimen mount 110. If the specimen is displaced too far to one side (as illustrated) the lever 16 can be moved about pivot 164 so that spigot 166 engages with metal mount 110 to push the specimen into the correct position (FIG. 8b). This is done while the specimen position is monitored on the computer screen. Since the stepper motor can be carefully controlled through manual switches, the specimen trajectory during rotation can be observed and the motor stopped when the specimen is maximally to one side. The specimen is then centred using the lever 16, and the process repeated until alignment of the specimen relative to the optical axis is complete. The lever 16 is organised so as to produce a "geared-down" movement to the specimen, which makes it easier to control the adjustment.

The pivot 164 is attached to the main motor stage. It is fixed to the stage by a support which ensures the spigot 166 is at the correct height to contact the metal mount, just below the magnet. This way, the spigot 166 remains at the correct height irrespective of the height chosen to image the specimen.

The apparatus described herein is suitable for 3D microscopy and also rotational microscopy for any purpose, on biological specimens and specimens from other fields such as material science.

When undertaking 3D microscopy, the refractive index should be uniform throughout the specimen. For biological tissue this is easily achieved by bathing the specimen in a clearing solvent. A specimen can be glued directly onto the metal mount, or embedded in a block of transparent matrix such as agarose, which is itself adhered to the mount. The clearing solvent then permeates the blocks as well as the specimen. BABB (a mixture of benzyl alcohol and benzyl benzoate) is suitable as a solvent.

For a specimen whose refractive index cannot be made uniform, or which is not transparent, the technique is still of use. The 3D surface shape of objects whose cross-sections are all convex (even if the whole 3D shape is not convex) can accurately be recreated from its rotating silhouette.

There are some applications where the raw data of the apparatus is useful. The series of images can be converted into a movie of the rotating object (i.e. the specimen). It is much easier to grasp the shape of a 3D object when it is viewed rotating than from a few static 2D images (many 3D reconstruction projects present their results as movies of a model rotating).

The apparatus is also suitable for undertaking 3D mapping of gene expression patterns (RNA and/or protein distribution) in biological tissue, whilst allowing the specimen to be used for other analysis after imaging. Specimen imaging using the apparatus is relatively quick, taking around 20 minutes. In contrast preparing, embedding, sectioning, mounting, staining and digitising real histological sections takes days and produces hundreds of digital 2D sections, but no guaranteed way to align them with each other to recreate the original 3D shape. The histological sections tend to stretch significantly, such that even if all the sections can be fitted onto each other to create a 3D shape, the final result will not accurately reflect the shape of the original specimen. However the results obtained using the apparatus are very similar to the real physical shape of the specimen, the only difference from physical sections being reduced resolution. As the data generated by the apparatus is genuinely 3D it can be virtually resectioned in any orientation, or rendered in 3D.

Figure 9:
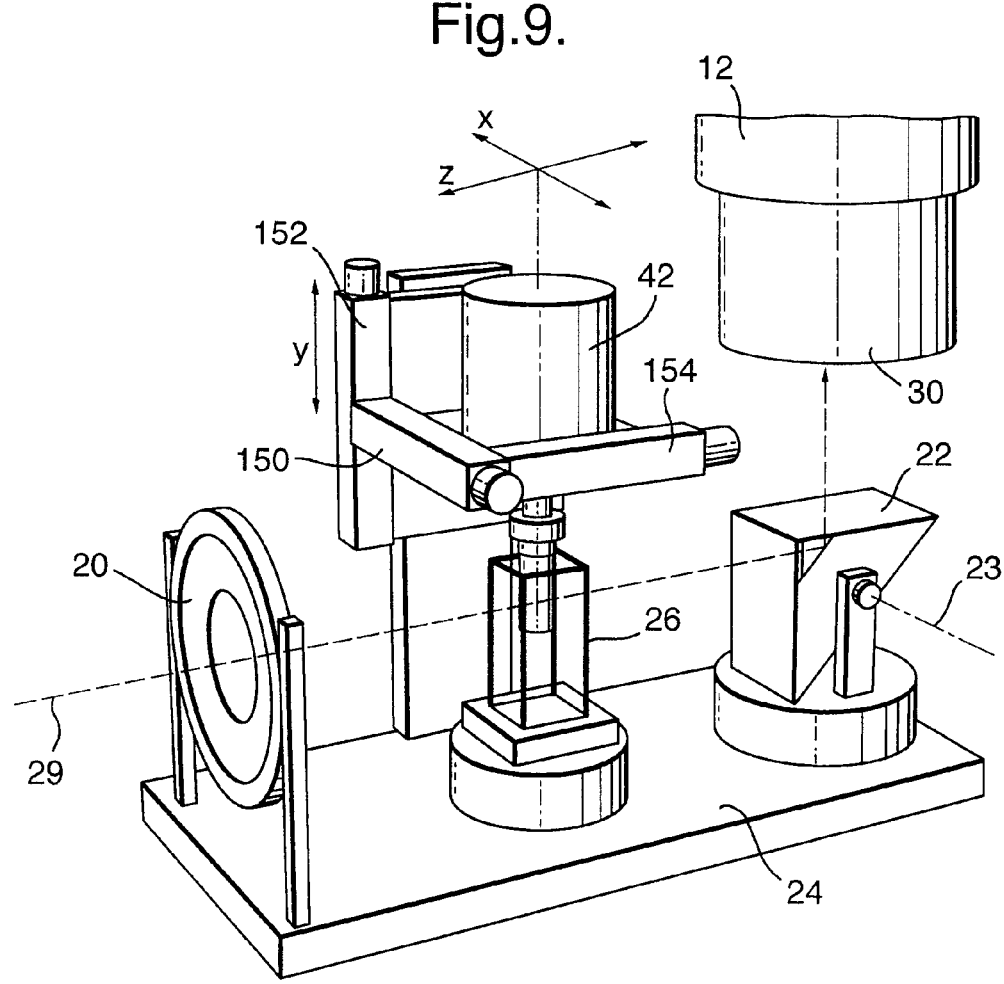
FIG. 9 is a perspective view of modified optical imaging apparatus according to the invention.

A modified construction of rotary stage is illustrated in FIG. 9 where parts corresponding to those of FIG. 1 bear the same reference numerals. In the rotary stage of FIG. 9, three-dimensional adjustment of the position of the stepper motor 42 is achieved by the use of three secondary stepper motors 150, 152, 154. No tilt adjuster for the motor 42 is present. Instead, the prism is capable of being manually adjusted by controlled tilting about a transverse horizontal axis 23. The important stepper motors are the motors 150 and 154. The motor 152 can be replaced by a manual vertical adjuster 40.

Figure 10:
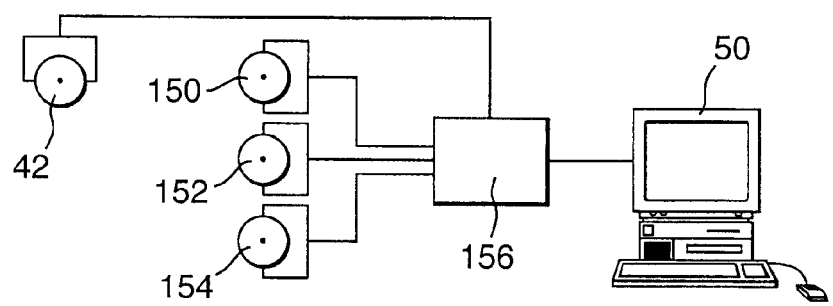
FIG. 10 is a diagram illustrating the apparatus of FIG. 9, FIGS. 11a, 11b, 11c, 12a, 12b, 13a, 13b and 14 illustrate positioning and viewing of the specimen image in the apparatus of FIG. 9, FIGS. 15 and 16 illustrate a collimated illumination means which may be used in the apparatus of FIG. 1 or FIG. 9, FIG. 17 indicates a way of selecting wavelength from a light source in the optical stage of FIG. 1 or FIG. 9.

The secondary stepper motors 150, 152, 154 allow sub-micron accuracy adjustment of the 3D position of the primary stepper motor 42, along the orientations labelled as x, y and z. These stepper motors 150, 152, 154 are controlled by the same computer which controls the primary motor 42. This is illustrated in FIG. 10 where the computer 50 drives the four motors through motor driving circuits 156. For the purposes of this document, the z-axis is considered parallel to the optical axis 29. Movements along this axis effectively alter the focus of the system. Movements along the other two axes alter which part of the specimen coincides with the centre of the optical axis 29.

The computer-controlled translation by the three secondary motors 150, 152, 154 has the following advantages:

1) It allows the region of interest (ROI) of the specimen to be maintained centrally within the field-of-view of the microscope. This is achieved in two ways:

(a) The ROI is maintained within the depth-of-focus of the microscope.
(b) It limits the "side-to-side" oscillatory movements of the ROI along the x-axis.

These two advantages allow much higher resolution imaging as compared to a system which has no such mechanism.

2) It is more accurate than the lever and spigot system of FIGS. 1 and 8.
3) It can be controlled completely by the computer (unlike the lever and spigot system), so the ROI can be easily defined "on-screen" within the software.
4) It allows the computer to calculate precise 3D coordinates for the ROI.
5) It allows different scans within the same specimen to be related to each other in 3D space.
6) This allows the computer to build-up a high resolution scan of a large specimen from multiple automatic scans of smaller regions at higher magnification (known as "tiling" or "patching").

Computer controlled x and z movements to maintain the ROI within the field-of-view are calculated as follows:

First, the software needs to calculate the positions of:
(a) The axis of rotation of the primary stepper motor 42 relative to the field-of-view.
(b) The ROI relative to the axis of rotation of the primary stepper.

Figure 11A:
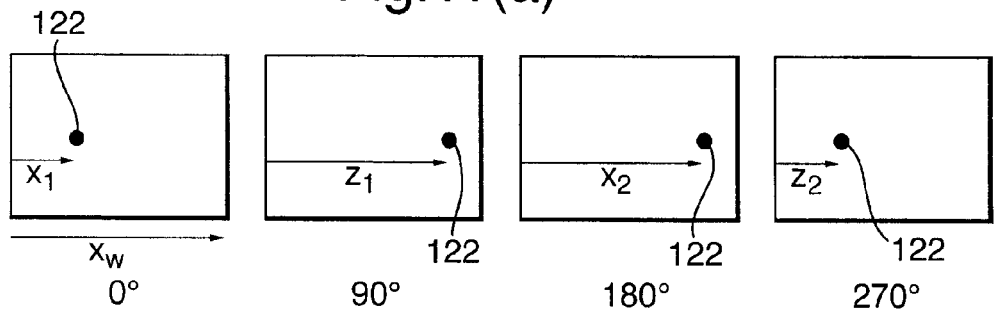
Figure 11B:
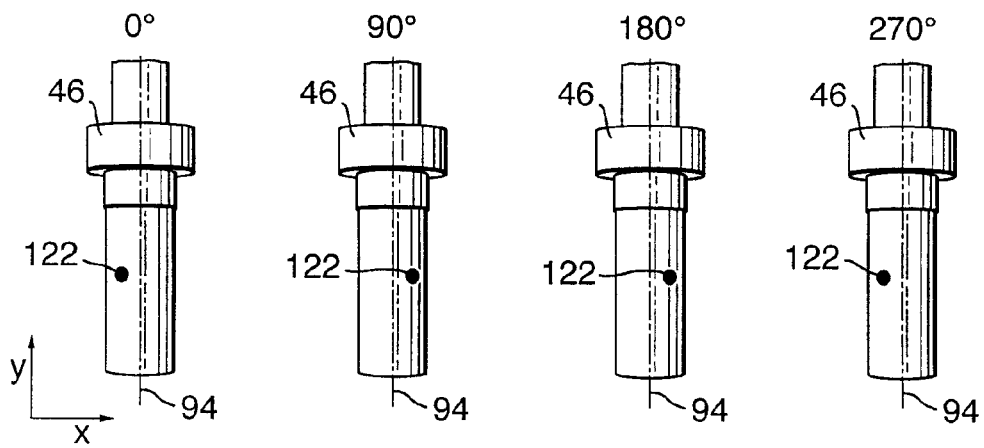
Figure 11C:
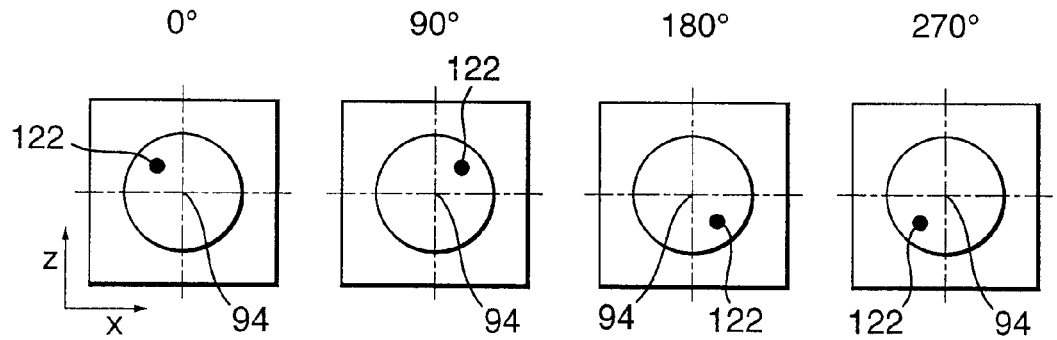

These two positions can be calculated from one operation. The magnification is set low enough such that during a full rotation the ROI stays within the field-of-view of the camera. The system is previously calibrated such that it is known how many pulses to the x-stepper motor correspond to a given displacement as measured in pixels on the computer screen. This relationship is determined for each magnification. The computer then presents the user with four images of the specimen, rotated to 0, 90, 180 and 270 degrees (as seen in FIGS. 11a to 11c). In FIG. 11a, each outer rectangle represents the imaging window on the computer screen and the spot represents the region of interest 122 of the specimen.

FIG. 11b shows views along the optical axis (as seen on the computer screen) for low magnification, and FIG. 11c shows plan views along the axis of rotation 94. The user then uses the computer mouse (or equivalent) to indicate where the ROI is in each image.

Figure 12A:
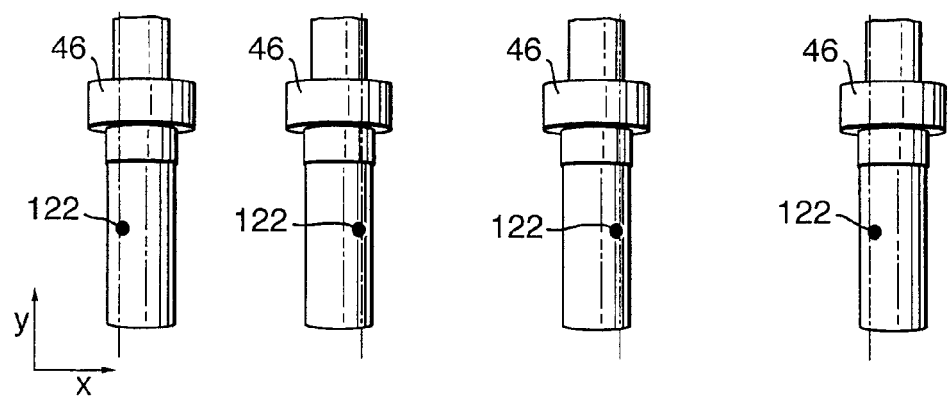
Figure 12B:
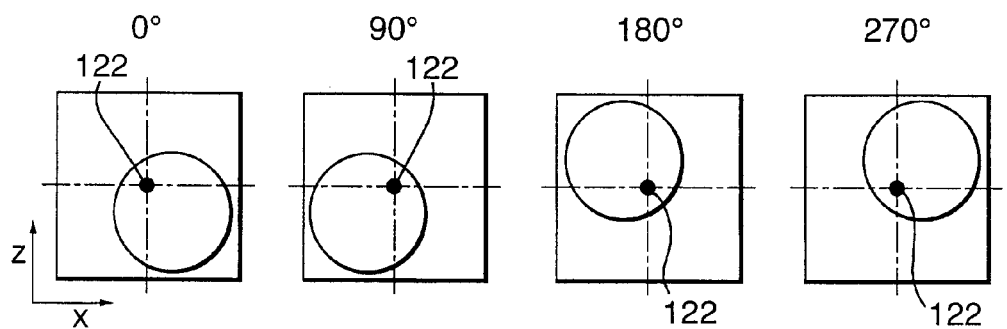

FIG. 12 shows how the positioning system can move the stepper motor 42 in both the x and z dimensions, and can therefore compensate for the ROI being off-centre. The x and z movements of the motor 42 are controlled by the computer to ensure that the ROI 122 remains in a fixed position, rotating around an effective axis of rotation.

In FIGS. 11a, 11b and 11c:

$\chi 1$=the x-position of the ROI at 0 degrees, converted to stepper motor units.

$\chi 2$=the x-position of the ROI at 180 degrees, converted to stepper motor units.

$\chi w$=the width of the imaging window, converted to stepper motor units.

The average $\chi 1$ and $\chi 2$ provides the position ($\chi s$) of the axis of rotation of the stepper motor relative to the imaging window ($\chi s$). The average of Z1 and Z2 provides a second estimate of this position ($\chi s=(\chi 1+\chi 2+Z1+Z2)/4$). The x-displacement which would be necessary to centre the axis of rotation of the stepper motor within the imaging window is:

X-displacement $(\chi d)=\chi w/2-(\chi 1+\chi 2+Z1+Z2)/4$

Figure 13A:
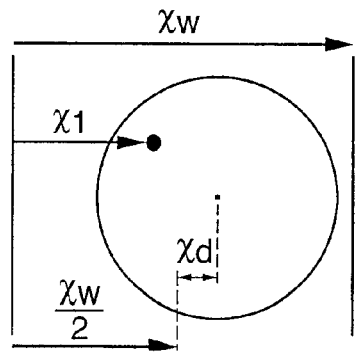
Figure 13B:
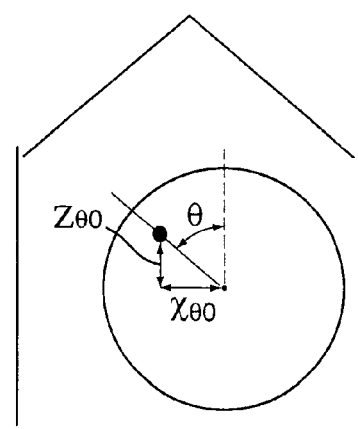

This is illustrated in FIGS. 13a and 13b.

In FIGS. 13a and 13b, the microscope views the specimen from the bottom of the diagram. The edges of the field-of-view therefore appear as two substantially parallel lines, which indicate the limits of what can be seen. The optical axis, which is the centre of this field-of-view, is shown as a vertical dashed line in FIG. 13a.

FIG. 13b shows the specimen at a rotational position of 0 degrees ($\alpha=0$). From the measurements described on the previous page ($\chi 1, \chi 2, Z1, Z2$) the x and z distances of the ROI from the axis of rotation of the primary stepper motor can easily be calculated. $\chi \alpha o$ is the x-distance when the rotational position (angle $\alpha$) is zero ($\chi \alpha o=(\chi 1-\chi 2)/2$). Similarly, $Z\alpha o$ can be calculated from the two measurements taken at $\alpha=90$ degree and $\alpha=270$ degrees, ($Z\alpha o=(Z1-Z2)/2$). The position of the ROI can then be converted from cartesian coordinates to polar coordinates where D is the distance of the ROI from the stepper motor axis, and $\theta$ is the angle of that line to the optical axis (or a line parallel to it), when $\alpha=0$ degrees.

$D$=square root of $(\chi \alpha o^2+Z\alpha o^2)\theta=\tan^{-1}(\chi \alpha o/Z\alpha o)$ Now, for any rotational position of the primary stepper motor ($\alpha$) the ROI can be positioned on the optical axis by movements of the secondary x z stepper motors, in which the total displacements (Xt and Zt) are calculated by:

$\chi t=\chi d+D \sin(\alpha+\theta)$, and $Zt=D.\cos(\alpha+\theta)$.

The 3-D shape of the region sampled from one OPT reconstruction is substantially a cylinder with a circular cross-section, whose axis of rotational symmetry is the effective axis of rotation used during imaging, and whose diameter and length are described by the width and height of the field-of-view. Since we can alternate between Cartesian and polar coordinates to describe positions within the specimen, and can relate the sizes of pixels to real distances within the specimen, we can easily calculate the position and shape of the sampled cylinder relative to any other scans made of the same specimen.

In 2-D imaging, a high-resolution image is often constructed by taking many high magnification images of small regions of the object, and then joining the smaller images together. This is often known as "tiling" or "patching". The computer-controlled XYZ stage allows the same approach to be applied to 3-D OPT imaging.

Figure 14:
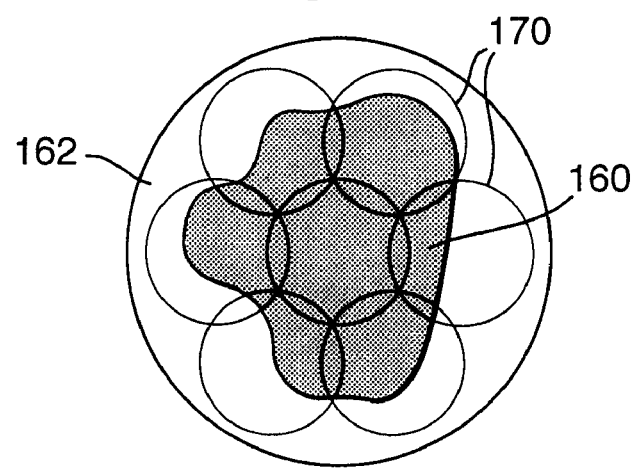

As described above, the sampled region from an OPT scan is a cylinder with circular cross-section. FIG. 14 illustrates, in plan view looking down along the axis 94, how a specimen 160 can be imaged in one scan 162 at low-resolution, or alternatively could be imaged by positioning seven high-resolution scans 170 such that every position within the specimen is contained within at least one sampled region. Since the individual sample regions have a circular cross-section, one efficient arrangement for covering a large region is to arrange the scans in a hexagonal pattern, with slight overlaps between adjacent scans. Different positions along the y-axis of the specimen can also be sampled using the y-axis stepper motor.

This tiling process can be completely controlled and performed by the computer.

For all specimens which are to be imaged in their entirety with one scan, calculating the position of the optimal sampled region can be done automatically without the need for the user to identify the ROI as previously described. Simple image-processing can find the outline or the centre of the specimen within test images during the alignment process, as follows:

1) Set magnification to low (can be done automatically using a computer-controlled microscope).
2) Take four images at 0, 90, 180 and 270 degrees rotation.
3) Calculate a histogram of each image to determine a suitable threshold level to distinguish the specimen from the background.
4) Calculate the position of the centre-of-mass of the specimen in each image.
5) Use these positions as the ROI measurements as previously described.
6) Apply the new displacements during any subsequent rotations.
7) Increase magnification.
8) Take four rotated images and determine whether magnification is too high (i.e. if edges of specimen are outside of the field-of-view).
9) If specimen still within field-of-view go back to step 4.
10) If edges of specimen are outside field-of-view reduce magnification to previous value.
11) Scan specimen.

Figure 15:
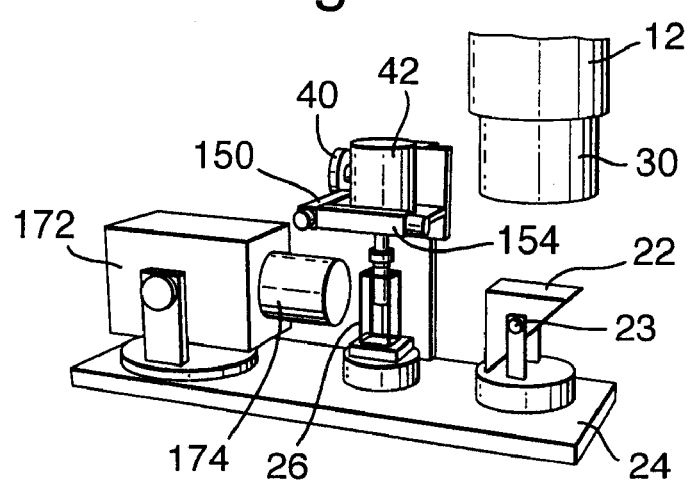
Figure 16:
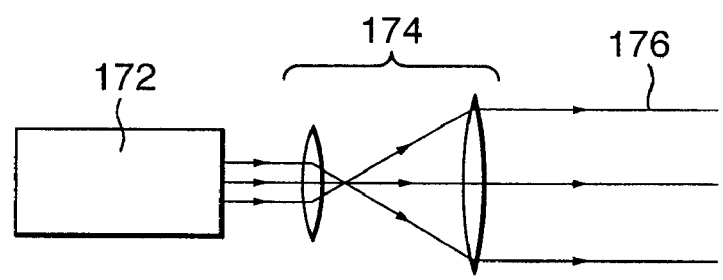

A collimated illumination means, which may be used in the rotary stage of FIG. 1 or FIG. 9, is illustrated in FIGS. 15 and 16.

A laser or other light source 172 is used in conjunction with a focussing means (either refractive lenses 174 or reflective mirrors) to generate a beam of light 176 in which all light rays are substantially parallel to the optical axis. FIG. 15 illustrates this device in relation to the remainder of the rotary stage which, in this example, has two stepper motors 150, 154 for computer-controlled adjustment in the x and z directions rexpectively. Vertical adjustment is effected manually by vertical adjuster 40. The lens 22 is capable of tilt adjustment about axis 23.

As a result of experiments it is clear that illuminating light which enters the specimen non-parallel to the optical axis introduces noise into the results. A collimated light source, where, all illuminating light rays are parallel to the optical axis, reduces this problem and therefore increases the quality of imaging.

Figure 17:
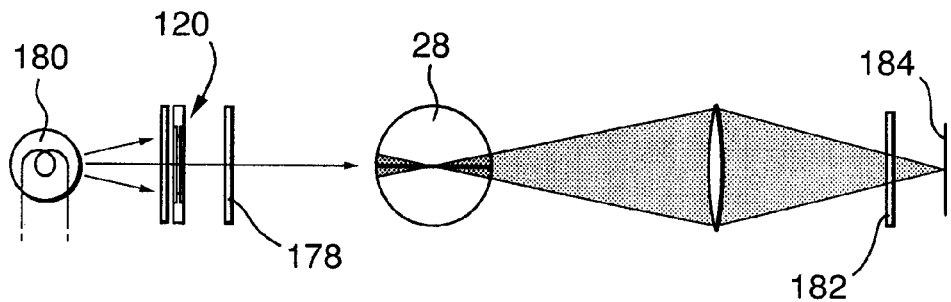

Referring to FIG. 17, a wavelength filter 178 is placed at some position between the light source 180 and the specimen 28. This may either consist of a series of different filters, each permitting the transmission of different range of wavelengths, which may be manually or automatically positioned in the lightpath. Or it may be an electronically-tunable filter.

Alternatively, two electronically-tunable liquid crystal filters may be used for fluorescent imaging to restrict the wavelengths of both the illumination light and the detected light, this possibility being illustrated by the second electrically-controlled filter 182 placed in front of a 2D array of light detectors 184.

A given chemical will absorb different wavelengths with varying degrees of efficiency. These differences can be represented as a spectrum (which describes the absorption for a large range of wavelengths). Most specimens consist of varying spatial distributions of different chemicals, and consequently different specimens are optimally imaged using different wavelengths (or combinations of wavelengths). The described filter system allows the user to alter which wavelengths are used to image a given specimen.

Similarly, fluorescent chemicals possess one spectrum which describes the efficiency of different wavelengths to excite them, and a second spectrum which describes the abundance of different wavelengths emitted on fluorescence. The use of two electronically-controlled filters produces (at least) a 2-D parameter space for the possible combinations of excitation and emission. Such a system allows the exploration of optimal combinations to distinguish between different chemicals. This allows the 3-D histology of biomedical samples to be imaged without the need for specific stains.

Figure 18:
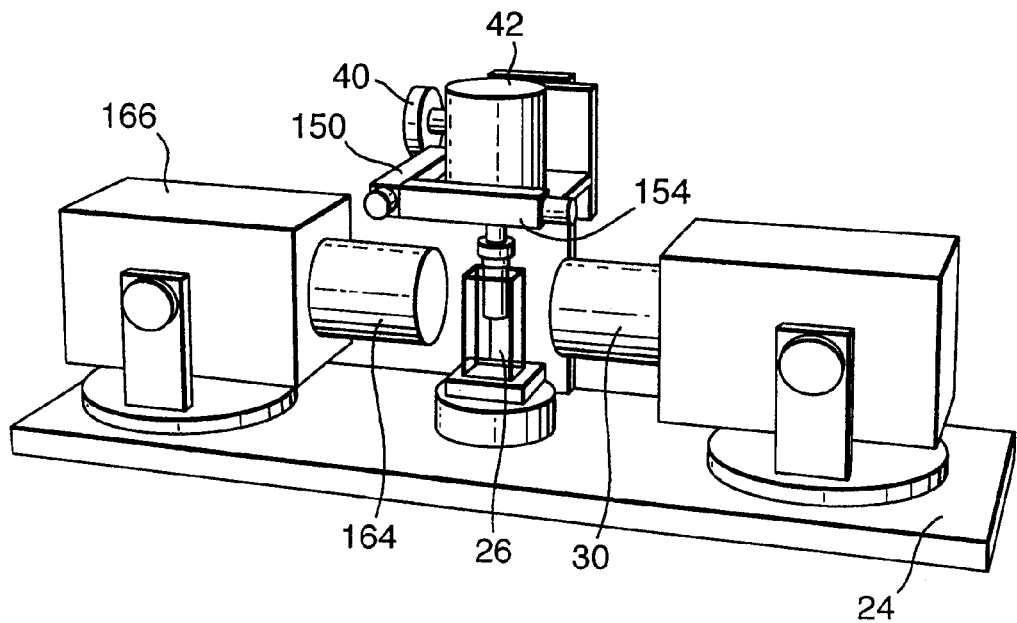
FIG. 18 illustrates a modification of the apparatus shown in FIG. 16.

It will be appreciated that a rotary stage according to the invention need not include a prism 22, and nor need the rotary stage be used with a standard vertical microscope. FIG. 18 illustrates a modification of the arrangement of FIG. 15. In FIG. 18 (where parts corresponding to those of FIG. 15 bear the same reference numerals), the light emanating from the chamber 26 enters microscope optics and a digital camera, giving a short working distance between the microscope objective 30 and the specimen.

The specimen may be positioned by the use of a translation stage carried by the shaft 44. The translation stage has manual or computer-controlled adjustment in the x and z directions.

The invention claimed is:

1. Optical Projection Tomography (OPT) apparatus including a rotary stage for use in imaging a specimen from a plurality of directions, the rotary stage comprising specimen support means including a rotatable member operative to rotate a specimen to be imaged about a vertical or substantially vertical axis of rotation transverse to an optical axis along which light is emitted from the specimen, wherein the specimen support means is disposed above a stationary imaging chamber for receiving the specimen immersed in optical imaging fluid within the chamber.

2. Optical Projection Tomography (OPT) apparatus according to claim 1, wherein the imaging chamber has at least one planar face which is perpendicular to the optical axis.

3. Optical Projection Tomography (OPT) apparatus according to claim 1 and including a prism positioned on the optical axis so as to receive light emitted by the specimen, the prism acting to deflect light through 90° to enable the light to be received by a microscope with a vertical optical axis.

4. Optical Projection Tomography (OPT) apparatus according to claim 3, wherein the prism is adjustable in position about a horizontal axis perpendicular to the optical axis which is also horizontal.

5. Optical Projection Tomography (OPT) apparatus according to claim 1, wherein the rotatable member is adjustable in position to adjust the axis of rotation about a horizontal adjustment axis perpendicular to the optical axis.

6. Optical Projection Tomography (OPT) apparatus according to claim 5, wherein the horizontal adjustment axis is below the lower end of the rotatable member to ensure that any horizontal adjustment causes minimum translation of the specimen.

7. Optical Projection Tomography (OPT) apparatus according to any claim 1, wherein the rotatable member is adjustable by translation along a direction aligned with the axis of rotation, to enable the specimen support means to be moved between a lowered operative position and a raised inoperative position in which specimens can be loaded into or unloaded from the rotary stage.

8. Optical Projection Tomography (OPT) apparatus according to claim 1, wherein the rotatable member is the output shaft of a stepper motor mounted on a platform adjustable in position.

9. Optical Projection Tomography (OPT) apparatus according to claim 1, wherein the lower end of the rotatable member is formed to enable the specimen to be hung or suspended, or to downwardly depend, from the lower end of the rotatable member.

10. Optical Projection Tomography (OPT) apparatus according to claim 9, wherein the rotatable member has, at or adjacent its lower end, a magnetic member for releasable attachment of the specimen by magnetic attraction.

11. Optical Projection Tomography (OPT) apparatus according to claim 1, wherein the specimen support means includes specimen positioning means for accurately positioning the specimen with respect to the axis of rotation.

12. Optical Projection Tomography (OPT) apparatus according to claim 11, wherein the specimen positioning means includes a lever pivotally mounted in the stage and operative to push a mounted specimen to achieve final positioning of the specimen.

13. Optical Projection Tomography (OPT) apparatus according to claim 11, wherein the specimen positioning means comprise two electric motors for computer-controlled adjustment of the rotatable member along two mutually perpendicular directions in a plane perpendicular to the axis of rotation.

14. Optical Projection Tomography (OPT) apparatus according to claim 11, wherein the specimen positioning means comprise manual or computer-controlled adjustment means for adjustment of a two-dimensional translation stage carried by the rotatable member, the translation stage providing adjustment in two mutually perpendicular directions in a plane perpendicular to the axis of rotation.

15. Optical Projection Tomography (OPT) apparatus according to claim 1 and including a collimated light source for producing a beam of light in which all light rays are substantially parallel to the optical axis and which, in use, illuminates the specimen.

16. Optical Projection Tomography (OPT) apparatus according to claim 1 and including a wavelength filter for restricting the wavelength of light illuminating the specimen.

17. Optical Projection Tomography (OPT) apparatus according to claim 1 and including two wavelength filters, namely a first filter for restricting the wavelength of light illuminating the specimen and a second filter for restricting the wavelength of light emanating from the specimen and before detection.

* * * * *